United States Patent
Kühn et al.

(10) Patent No.: US 7,923,019 B2
(45) Date of Patent: Apr. 12, 2011

(54) ANTIBIOTIC/S CONTAINING BONE SUBSTITUTE MATERIAL WITH SUSTAINED ACTIVE SUBSTANCE RELEASE

(75) Inventors: Klaus-Dieter Kühn, Marburg (DE); Sebastian Vogt, Erfurt (DE)

(73) Assignee: Heraeus Kulzer GmbH, Hanua (DE)

( * ) Notice: Subject to any disclaimer, the term of this patent is extended or adjusted under 35 U.S.C. 154(b) by 601 days.

(21) Appl. No.: 11/294,001

(22) Filed: Dec. 5, 2005

(65) Prior Publication Data

US 2006/0127444 A1 Jun. 15, 2006

(30) Foreign Application Priority Data

Dec. 15, 2004 (DE) .......... 10 2004 060 666

(51) Int. Cl.
*A61K 33/42* (2006.01)
*A61F 2/00* (2006.01)

(52) U.S. Cl. .......... 424/423; 424/602
(58) Field of Classification Search .......... 424/423, 424/602; 623/23.51, 23.61–23.63

See application file for complete search history.

(56) References Cited

U.S. PATENT DOCUMENTS

| 5,055,307 | A | | 10/1991 | Tsuru et al. |
| 5,149,368 | A | * | 9/1992 | Liu et al. .......... 424/602 |
| 5,614,206 | A | | 3/1997 | Randolph et al. |
| 5,681,873 | A | | 10/1997 | Norton et al. |
| 5,756,127 | A | | 5/1998 | Grisoni et al. |
| 5,807,567 | A | | 9/1998 | Randolph et al. |
| 6,224,635 | B1 | * | 5/2001 | Ricci et al. .......... 623/23.62 |
| 6,652,887 | B1 | | 11/2003 | Richelsoph et al. |
| 2002/0110541 | A1 | | 8/2002 | Petersen |
| 2002/0182251 | A1 | * | 12/2002 | Vogt et al. .......... 424/464 |
| 2002/0197315 | A1 | | 12/2002 | Haggard et al. |
| 2003/0161858 | A1 | * | 8/2003 | Lidgren .......... 424/423 |

FOREIGN PATENT DOCUMENTS

| DE | 199 53 771 | C1 | 6/1999 |
| DE | 101 14 244 | A1 | 10/2002 |
| DE | 101 14 245 | A1 | 10/2002 |
| DE | 101 14 364 | A1 | 10/2002 |
| DE | 10 27 914 | A1 | 1/2004 |
| DE | 10 27 935 | A1 | 1/2004 |
| DE | 10 27 938 | A1 | 1/2004 |
| EP | 0 985 413 | A1 | 3/2000 |
| EP | 1 374 854 | A1 | 1/2004 |
| EP | 1 374 923 | A2 | 1/2004 |
| WO | 01 76649 | A1 | 10/2001 |

OTHER PUBLICATIONS

Darley et al. Journal of Antimicrobial Chemotherapy. 2004; 53: 928-935.*

* cited by examiner

*Primary Examiner* — Shanon A Foley
(74) *Attorney, Agent, or Firm* — Norris McLaughlin & Marcus, P.A.

(57) ABSTRACT

Antibiotic/s containing bone substitute material is described which is characterized in that it is composed of a compacted mixture of granules of calcium sulfate dihydrate, calcium carbonate and at least one representative of the aminoglycoside antibiotics, lincosamide antibiotics, glycopeptide antibiotics, macrolide antibiotics, ketolide antibiotics, the nitroimidazoles, the fluorochinolone antibiotics and the oxazolidinone antibiotics, the steroid antibiotics, the antiseptic agents and the fungicidal/fungistatic antibiotics which are partly or entirely sheathed with a layer of glycerol tripalmitate and/or glycerol tristearate and/or glycerol trilaurate and/or 1-hexadecyl alcohol which connects the granules with each other.

6 Claims, No Drawings

ANTIBIOTIC/S CONTAINING BONE SUBSTITUTE MATERIAL WITH SUSTAINED ACTIVE SUBSTANCE RELEASE

BACKGROUND OF THE INVENTION

1. Field of the Invention

Subject of the invention is an antibiotic/s containing bone substitute material with sustained active substance release.

2. Description of Related Art

Osteomyelitis is an infection of the bone tissue which is very difficult to therapy. Normally, the treatment comprises the debridement of infected bone areas. Subsequent localized antibiotics therapy has proven well, with non-resorbable Septopal® chains or with gentamicin-containing collagen fleeces. Here, gentamicin is locally released in high doses which kills off the remaining bacterial pathogens. Desirable is a bone substitute material which, on one hand, can locally release antibiotics and, on the other hand, will further bone growth and which has a placeholder function.

The use of calcium sulfate dihydrate as a bone substitute material has been known for a long time (E. Martin: Zur Ausfüllung von Knochenhöhlen mit totem Material. Zentalb Chir 21 (1894) 193-200; E. Edberg: Some experiences of filling osteous cavities with plaster. Acta Chir Scand 67 (1930) 313-319; J. O. Hollinger, J. Brekke, E. Kruskin, D. Lee: Role of bone substitutes. Clin Orthop 324 (1996) 55-65).

The US 2002110541, U.S. Pat. No. 5,807,567, US 2002197315, U.S. Pat. No. 6,652,887, U.S. Pat. No. 5,756,127 and U.S. Pat. No. 5,614,206 describe bone substitute materials which essentially consist of a mixture of α and β calcium sulfate and are to be used as drug delivery systems for pharmaceutically active substances. These bone substitute materials release the major amount of the incorporated active substance in the first hours after introduction of the material into an aqueous solution and, thereafter, only minor amounts of active substance will be released over a period of several days.

DE 19953771 discloses a bone substitute material consisting of a mixture of calcium sulfate dihydrate and nano-particular hydroxyl apatite. Moulds of this material have a high interior surface and can be impregnated with aqueous antibiotic solutions. Such treated moulds will have a more or less sustained release action. The major amount of the antibiotic will be released in the first hours. The sustained release is due to the adsorption of the active substance on the interior surface of the mould.

DE 10114244, DE 10114245, DE 10114364, DE 10227914 or DE 10227938 describe active substance formulations or, respectively, methods for the manufacture of these active substance formulations which rely on the formation or, respectively, use of active substance salts of low solubility in water. Thus, DE 10227914 discloses a pharmaceutical preparation with a sustained active substance release, consisting of mixtures of powdered teicoplanin and at least one powdered, water-soluble salt form of gentamicin, clindamycin, vancomycin, moxifloxacin, and ciprofloxacin and an inorganic auxiliary substance and/or organic auxiliary substance. Proposed as auxiliary substances are, inter alia, calcium carbonate, calcium sulfate dihydrate, tricalcium phosphate and hydroxyl apatite. The pharmaceutical preparation will be used in the form of pellets, moulds, fibers/threads and granulates as implant material.

DE 10227935 describes an antibiotic coating of porous bodies and their utilization. In the pore system of non-metallic and metallic porous bodies, a coating is provided of at least one antibiotic salt—with low solubility in water—from the group of the fatty acid salts and dodecyl sulfates of netilmicin, sisomycin, gentamicin, clindamycin, amikacin, kanamycin, tobramycin, ciprofloxacin, and vancomycin. The coating is also applied on porous powders, porous granulates, porous moulds and porous layers of compact bodies. The antibiotically coated bodies are to be used as implants.

U.S. Pat. No. 5,055,307 proposes granulates for sustained active substance release. These granulates are formed of a calcium phosphate with a substance volume ratio of Ca to P from 1.3 to 1.8, having a porosity of 0.1% to 70% and a specific surface of 0.1 $m^2/g$ to 50 $m^2/g$. The pore size is in the range from 1 nm to 10 μm. The granulates are formed in a calcination process in a temperature range from 200° C. to 1,400° C. Subsequently, the granulates are impregnated with an active substance. It is also possible to drench the granulates with a polymer solution and separate a polymer layer on the granulates.

SUMMARY OF THE INVENTION

The invention is based on the objective of developing an inexpensive antibiotic/s containing bone substitute material which is easy to manufacture and has a sustained active substance release.

The problem was solved according to the invention as described herein. An antibiotic/s containing bone substitute material was found which is characterized in that it is composed of a compacted mixture of granules of calcium sulfate dehydrate, of calcium carbonate and at least one representative of the aminoglycoside antibiotics, lincosamide antibiotics, glycopeptides antibiotics, macrolide antibiotics, ketolide antibiotics, nitroimidazoles; fluorochinolone antibiotics and the oxazolidinone antibiotics, the steroid antibiotics, and the fungicidal/fungistatic antibiotics which are partly or entirely sheathed with a layer of glycerol tripalmitate and/or glycerol tristearate and/or glycerol trilaurate and/or 1-hexadecyl alcohol which connects the granules with each other. That means the individual granules are partly or entirely sheathed with a layer of glycerol tripalmitate and/or glycerol tristearate and/or glycerol trilaurate and/or 1-hexadecyl alcohol. The layer has a preferred layer thickness of smaller than 100 μm.

DETAILED DESCRIPTION OF THE INVENTION

Surprisingly, the moulds according to the invention provide a sustained release of the antibiotics over a period of time ranging from several days to two weeks. The term compacted mixture means that the granules are pressed to form a compact body which has no macropores of pore diameters larger than 50 μm. To this end, it should be pressed with a high pressing force of at least 30 kN (for example with a mould of a diameter of approx. 6 mm). The compacted structure influences the diffusion of the active substances from the inside of the material to the surface. Instead of glycerol trilaurate, glycerol tripalmitate and glycerol tristearate, the following can also be used: glycerol dilaurate, glycerol trimyristate, glycerol dimyristate, glycerol dipalmitate, glycerol distearate, beeswax, tallow, hard grease or hydrated vegetable oils.

Preferred as components of the bone substitute materials according to the invention are the active substances of gentamicin, tobramycin, netilmicin, sisomycin, amikacin, lincosamin, clindamycin, teicoplanin, vancomycin, ramoplanin, erythromycin, telithromycin, azithromycin, ciprofloxacin, moxifloxacin, linezolid, metronidazol, tinidazol, fluconazol, amphotericin B, nystatin, griseofulvin, fusidin acid, fosfomycin, rifampicin, chloramphenicol, chlorhexidine, polyhexanide or their individual substances or their mixtures. The active substances can be used as salts easily soluble in water or also as salts with low solubility in water. Therefore, it is also within the purpose of the invention that the salts of these antibiotics with low solubility in water are incorporated in the bone substitute materials according to the invention. Thus, for example, gentamicin palmitate, tobramycin palmitate and gentamicin dodecyl sulfate.

Furthermore, it is advantageous that the bone substitute material has the form of cylindrical or facetted pellets or the form of granulate with a particle diameter of 100-2,500 µm having, on the surface, a closed layer of glycerol tripalmitate and/or glycerol tristearate and/or glycerol trilaurate and/or 1-hexadecyl alcohol.

It is expedient that the calcium carbonate is partly or entirely replaced by β-tricalcium phosphate, calcium hydrogen phosphate, calcium hydrogen phosphate dihydrate, magnesium carbonate, trimagnesium phosphate, magnesium hydroxide, magnesium oxide.

It is moreover expedient that a composition will be preferred with
50.0-90.0 percent by mass of calcium sulfate dihydrate,
1.0-40.0 percent by mass of calcium carbonate,
1.0-40.0 percent by mass of glycerol tripalmitate and/or glycerol tristearate and/or glycerol trilaurate and/or 1-hexadecyl alcohol, as well as
0.1-10.0 percent by mass of at least one representative of the aminoglycoside antibiotics, the lincosamide antibiotics, macrolide antibiotics, ketolide antibiotics, the nitroimidazoles, the fluorochinolone antibiotics, oxazolidinone antibiotics, steroid antibiotics, antiseptic agents and the fungicidal/fungistatic antibiotics.

According to the invention, moulds of the bone substitute material are produced which preferably have the form of spheres, spherical bodies, rings or cylinders, if necessary with a bore-through.

The invention is explained by the following examples without, however, limiting it.

EXAMPLE 1

In a roller mill are ground together 179.91 g calcium sulfate dihydrate (Merck), 44.98 g calcium carbonate (Fluka) and 6.88 g gentamicin sulfate (AK545, equivalent to 3.75 g gentamicin base). Subsequently, this mixture is mixed with a solution—temperature-adjusted to 60° C.—of 18.23 g tripalmitin (glycerol tripalmitate from Fluka) in ethanol. A mixture of a pulpy consistency is formed. After the ethanol is evaporated, the hardened mixture is broken into granulate and screened. This granulate (grain fraction 63-500 µm) will be pressed in a standard eccentric pelleting machine to pellets with a mass of 250 mg, a diameter of 6 mm and a height of 4.5 mm.

EXAMPLE 2

In a roller mill are ground together 176.51 g calcium sulfate dihydrate (Merck), 44.13 g calcium carbonate (Fluka) and 11.47 g gentamicin sulfate (AK 545, equivalent to 6.25 g gentamicin base). Subsequently, this mixture is mixed with a solution—temperature-adjusted to 60° C.—of 17.89 g tripalmitin (glycerol tripalmitate of Fluka) in ethanol. A mixture of a pulpy consistency is formed. After the ethanol is evaporated, the hardened mixture is broken into granulate and screened. This granulate (grain fraction 63-500 µm) will be pressed in a standard eccentric pelleting machine to pellets with a mass of 250 mg, a diameter of 6 mm and a height of 4.5 mm.

EXAMPLE 3

In a roller mill are ground together 172.11 g calcium sulfate dihydrate (Merck), 43.03 g calcium carbonate (Fluka), 7.81 g gentamicin sulfate (Fujian, AK 640, equivalent to 5.0 g gentamicin base) and 5.77 g clindamycin hydrochloride (Upjohn, AK867, equivalent to 5.0 g clindamycin base). Subsequently, this mixture is mixed with a solution—temperature-adjusted to 60° C.—of 21.28 g tripalmitin (glycerol tripalmitate from Fluka) in ethanol. A mixture of a pulpy consistency is formed. After the ethanol is evaporated, the hardened mixture is broken into granulate and screened. This granulate (grain fraction 63-500 µm) will be pressed in a standard eccentric pelleting machine to pellets with a mass of 250 mg, a diameter of 6 mm and a height of 4.5 mm.

Release Trials

Six pellets each of the Examples 1 and 2 were stored in 20 ml distilled water at 37° C. Every day, 15 ml of the release medium was removed and replaced by fresh distilled water. The released gentamicin was determined in the removed medium. A TDX analyzer of company Abbott was used to determine the released gentamicin. In calculating the released gentamicin volume, the incomplete removal of the release medium as of the first day was also taken into account. The respectively released mass of gentamicin base of 6 pellets was presented in the following table as a function of the storage period of the sample bodies in the release medium. After day 11, the release trials were terminated.

| | Gentamicin base release of 6 pellets [µg] Time | | | | | | | | | |
|---|---|---|---|---|---|---|---|---|---|---|
| | 1 d | 2 d | 3 d | 4 d | 7 d | 8 d | 9 d | 10 d | 11 d | 11 d |
| Pellets Example 1 | 7,514 | 6,638 | 4,440 | 2,019 | 2,074 | 326 | 244 | 219 | 219 | 204 |
| Pellets Example 2 | 13,877 | 12,388 | 6,781 | 3,668 | 2,617 | 369 | 334 | 206 | 207 | 256 |

What is claimed is:

1. Antibiotic/s containing bone substitute material, comprising a mixture of granules compacted in a mold with a pressing force of at least 30 kN of the following components:
   calcium sulfate dihydrate,
   and at least one member selected from the group consisting of calcium carbonate, β-tricalcium phosphate, calcium hydrogen phosphate, calcium hydrogen phosphate dihydrate, magnesium carbonate, trimagnesium phosphate, magnesium hydroxide and magnesium oxide,
   and at least one member selected from the group consisting of aminoglycoside antibiotics, lincosamide antibiotics, glycopeptide antibiotics, macrolide antibiotics, ketolide antibiotics, nitroimidazoles, fluoroquinolone antibiotics, oxazolidinone antibiotics, steroid antibiotics, and fungicidal/fungistatic antibiotics, with the granules being partly or entirely sheathed with a layer of one or more substances selected from the group consisting of glycerol tripalmitate, glycerol tristearate, glycerol trilaurate and 1-hexadecyl alcohol which connects individual granules with each other, wherein the compacted mixture has no macropores of pore diameters larger than 50 µm.

2. Antibiotic/s containing bone substitute material according to claim 1, having the form of pellets or the form of granulate from granules with a particle diameter of 100 to 2,500 µm, with the granules being partly or entirely sheathed with a layer of one or more substances selected from the group consisting of glycerol tripalmitate, glycerol tristearate, glycerol trilaurate, and 1-hexadecyl alcohol which connects individual granules with each other.

3. Antibiotic/s containing bone substitute material according to claim 2, comprising cylindrical or facetted pellets.

4. Antibiotic/s containing bone substitute material according to claim 1, comprising a composition of:

50.0-90.0 percent by weight of calcium sulfate dihydrate,
1.0-40.0 percent by weight of calcium carbonate,
1.0-40.0 percent by weight of one or more substances selected from the group consisting of glycerol tripalmitate, glycerol tristearate, glycerol trilaurate and 1-hexadecyl alcohol, and
0.1-10.0 percent by weight of at least one member selected from the group consisting of aminoglycoside antibiotics, lincosamide antibiotics, glycopeptide antibiotics, macrolide antibiotics, ketolide antibiotics, the nitromidazoles, fluoroquinolone antibiotics, oxazolidinone antibiotics, antiseptic agents, steroid antibiotics and fungistatic/fungicidal antibiotics.

5. Antibiotic/s containing bone substitute material according to claim 1, which comprises at least one antibiotic selected from the group consisting of gentamicin, tobramycin, netilmicin, sisomycin, amikacin, lincosamin, clindamycin, teicoplanin, vancomycin, ramoplanin, erythromycin, telithromycin, azithromycin, ciprofloxacin, moxifloxacin, linezolid, metronidazol, tinidazol, fluonazol, amphotericin B, nystatin, griseofulvin, fusidin acid, fosfomycin, rifampicin, chloramphenicol, chlorhexidine, and polyhexanide.

6. A process for preparing antibiotic/s containing bone substitute material according to claim 1, comprising:
a) forming a mixture of granules of the components; and
b) forming a compacted mixture of the granules.

* * * * *